United States Patent [19]
Yu

[11] Patent Number: 5,190,532
[45] Date of Patent: Mar. 2, 1993

[54] CANNULA CAP

[76] Inventor: Wing-Kwong S. Yu, 2966 Crystal Creek Dr., San Jose, Calif. 95133

[21] Appl. No.: 880,696

[22] Filed: May 8, 1992

[51] Int. Cl.$^5$ .............................................. A61M 5/32
[52] U.S. Cl. ...................................... 604/192; 604/263
[58] Field of Search ................ 604/192, 193, 187, 263

[56] References Cited

U.S. PATENT DOCUMENTS

| | | | |
|---|---|---|---|
| 3,108,591 | 10/1963 | Kolbas | 604/193 |
| 4,747,839 | 5/1988 | Tarello et al. | |
| 4,880,413 | 11/1989 | Giuffre et al. | 604/192 |
| 5,000,742 | 3/1991 | Morrison | 604/263 X |
| 5,002,536 | 3/1991 | Thompson et al. | 604/192 |

FOREIGN PATENT DOCUMENTS

| | | |
|---|---|---|
| 728465 | 2/1966 | Canada . |
| 61444 | 5/1955 | France . |
| 2311556 | 12/1976 | France . |

*Primary Examiner*—John D. Yasko
*Attorney, Agent, or Firm*—Richard C. Litman

[57] ABSTRACT

A cannula cap is provided with a peripheral flange about its opening through which a needle is inserted. If the cannula cap is to be reinserted over the needle after the syringe is used, the flange provides protection to the user's fingers by blocking the needle from sticking the user as he or she is reinserting the cannula cap over the syringe needle.

4 Claims, 2 Drawing Sheets

CANNULA CAP

BACKGROUND OF THE INVENTION

1. Field of the Invention

The present invention relates to hypodermic syringe needle caps which prevent the needle from being contaminated by the ambient environment whenever the needle cap is located thereover, while also preventing a user of the hypodermic syringe, such as a nurse or doctor, from being accidently stuck by the needle. Further, this invention relates to those hypodermic syringe needle safety caps which may be reinserted over a hypodermic needle in a safe manner, without any danger of the user's fingers being stuck by the hypodermic needle in the process. More particularly, this invention incorporates a plastic protective peripheral flange around the opening through which the hypodermic needle enters the needle cap, wherein the protective flange blocks the needle from coming in contact with any portion of the user's fingers holding the needle cap.

2. Description of the Prior Art

Hypodermic syringes have a cylindrical barrel with a large open end through which a plunger is placed and a small open end on which a hub is placed. The cannula needle is affixed to the hub. A cannula cap or sheath is secured over the needle after the needle is sterilized. In this manner, the needle is maintained sterile until used by the medical attendant or doctor.

The cannula cap is air tight and may be made from plastic. By preventing contaminates from the ambient environment from reaching the needle, the cannula needle is maintained sterile. Further, the cannula cap helps prevent the needle from being broken as well as the needle from sticking a user handling the syringe.

French patent no. 61,444 dated May 4, 1955 discloses a cannula cap having a conical shaped body with a front open end and a closed back end (see FIG. 7). The forward most portion of the cannula cap engaging the hub of the syringe is located at the front end thereof. A peripheral flange around the front open end extends radially out from a longitudinal center axis of the cannula cap.

French patent no. 2,311,556 dated Dec. 17, 1976 discloses a cannula cap having an elongated body with a front open end and a closed back end where the forward most portion of the cannula cap engaging the hub of the syringe is located at the front end thereof.

Canadian patent no. 728,465 issued Feb. 22, 1966 to William H. Gottschalk discloses a sheath or cap molded out of thermoplastic material. It is provided with a front open end into which the cannula is inserted and a closed back end, whereby the front open end snugly engages the outer surface of the needle mounting collar.

U.S. Pat. No. 4,747,839 issued May 31, 1988 to William R. Tarello et al discloses a cannula cap with an open front end and a back closed end whereby the front open end is affixed to the hub of the syringe.

None of the above inventions and patents, taken either singularly or in combination, is seen to describe the instant invention as claimed.

SUMMARY OF THE INVENTION

The present invention is an improved hypodermic needle cap which provides greater safety to the user when the hypodermic needle cap is being placed back over the hypodermic needle. After the hypodermic syringe has been used by a user, such as a doctor or nurse, the user may wish to place the hypodermic needle cap back over the needle. The user may stick his or her fingers during this recapping process. The hypodermic needle cap of the present invention is designed with a peripheral flange which extends from the front open end thereof in a radial direction from a longitudinal center axis of the cap. The flange extends out a distance from the front open end sufficient enough to protect the fingers of the user during the recapping process.

With the design of the present invention, should the user miss placing the needle through the front open end, the peripheral flange about the front open end would block the needle from sticking the fingers of the user gripping the hypodermic needle cap. The peripheral flange has a front surface which is perpendicular to the longitudinal center axis of the cap, thereby providing a safety region behind the peripheral flange. The safety region should be large enough to protect all portions of the user's fingers in contact with the safety cap.

Behind the peripheral flange of the cannula cap, is a funnel region of the cap, through which the needle is inserted during the recapping process. Behind the funnel region is a needle housing region which incases the needle to prevent the needle from being contaminated by the ambient environment while also preventing a user from being accidently stuck by the needle when handling the syringe. The needle housing region engages the hub of the syringe at the opening thereof to provide an airtight attachment for the cannula cap over the needle so the needle remains sterilized.

In the preferred embodiment, the needle housing region is conically shaped with each portion of the inner cavity as well as the outer perimeter thereof decreasing in circular diameter as the portions progress from the opening of the housing region to the back closed end of the cannula cap, which is also the back end of the needle housing region. Further, in the preferred embodiment the housing region, as well as the rest of the cannula cap, is made of plastic which the needle can not penetrate.

The funnel region begins at the opening of the cannula cap. The region is designed to guide the needle into the opening of the needle housing region. The funnel region has smoothly rounded inner surfaces which would guide the needle toward the longitudinal center axis if the needle is not being inserted close enough down the center of the opening of the cannula cap. As long as the needle is being inserted close enough down the center of the cannula cap opening so as to enter the opening of the needle housing region, the needle will not contact the inner surface of the funnel region. However, if the needle is not inserted in this manner, the needle will hit the smooth rounded surface of the funnel region and would be deflected towards the longitudinal center axis of the cannula cap.

The outer surface of the funnel region forms a smooth concave surface between the peripheral flange of the opening of the cap and the needle housing region of the cap. This region allows the user's fingers to easily grip the cap when reinserting the cap over the needle of the syringe. As long as the users index finger and thumb grip the cap about the funnel region, the portions of the user's index finger and thumb in contact with the cap are protected from the needle. For example, if the user tries to reinsert the needle into the cap by gripping the cap around peripheral flange of the cap opening, his or her fingers are not being protected by the peripheral flange.

Accordingly, it is a principal object of the invention to provide a cannula cap which protects the user's fingers from being stuck by the needle when the cap is being reinserted over the needle.

It is another object of the invention to provide a peripheral flange about the opening of the cannula cap through which the needle is to be reinserted so as to provide a safe region behind the peripheral flange.

It is a further object of the invention to provide a conically shaped needle housing region of the cannula cap to prevent the cannula needle of the syringe from being contaminated before it is used, e.g., while in storage.

It is still another object of the present invention to provide a conically shaped needle housing region of the cannula cap to prevent the cannula needle of the syringe from accidently sticking a user before or after it is used, e.g., while it is being moved from one location to another.

It is still another object of the present invention to provide an opening of the needle housing region which snugly and securely attaches over the hub of the syringe so as to provide an airtight fitting thereover to keep the needle sterile before it is used.

It is still another object of the present invention to provide a funnel region inner surface between the opening of the cannula cap and the opening of the needle housing region so as to guide the needle which impinges thereon towards the opening of the needle housing region.

It is still another object of the present invention to provide a funnel region outer surface between the back portion of the peripheral flange of the cannula cap opening and the outer surface of the conically shaped needle housing region where the user's fingers may easily and safely grip the cannula cap when reinserting the cap over the cannula needle of the syringe.

Still another object of the invention is to make the cannula cap out of plastic so as to be impenetrable if the needle should impact any portion thereof.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
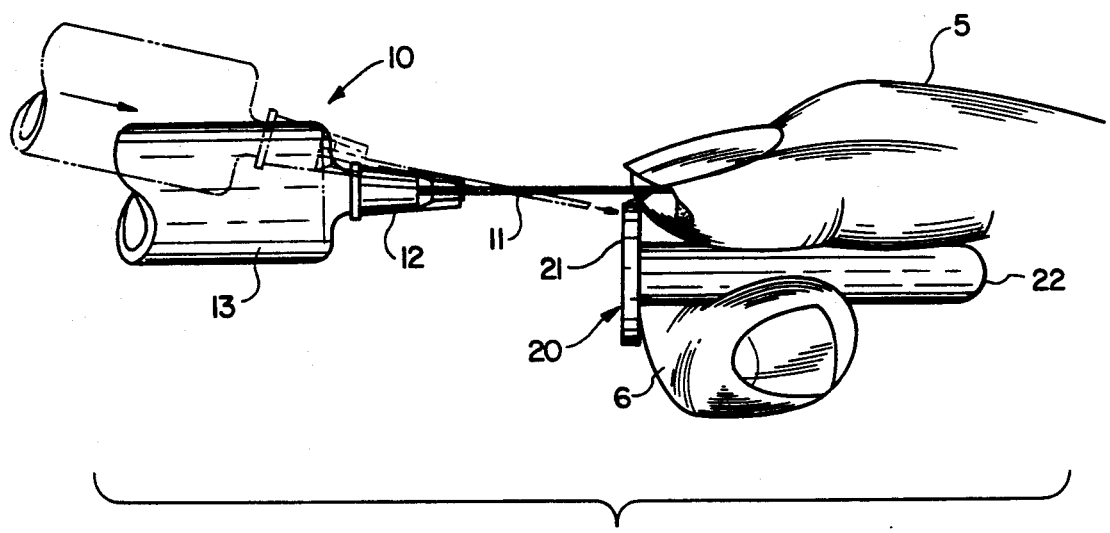
FIG. 1 is an environmental view of the prior art cannula cap showing the dangers associated therewith upon the user attempt to reinsert the cap over the syringe needle.

As shown in FIG. 1, the cannula cap 20 of the prior art fails to provide adequate protection to a user's fingers 5 and 6 as the user is attempting to place the cap 20 back over the cannula needle 11 of the syringe. The user's fingers can be stuck by the needle 11 easily. If the user misses the opening of the cannula cap 20 when reinserting the cap over the needle, the user's fingers can be easily stuck by the needle since the user's fingers 5 and 6 are only slightly protected by the average cannula cap of the prior art.

For example, as shown in FIG. 1, the cannula cap 20 has a peripheral flange 21 about the opening of the needle housing region 22. The user's thumb 5 is only partly protected behind the flange 21. The region of safety behind the flange 21 is indicated by a region S1. The thumb is stuck by the needle 11 of the syringe 10, as indicated in FIG. 1. The syringe 10 is a typical prior art syringe with a hub 12 attaching a needle 11 to a barrel 13. The portion of the thumb stuck by the needle is outside of the protective region S1.

Figure 2:
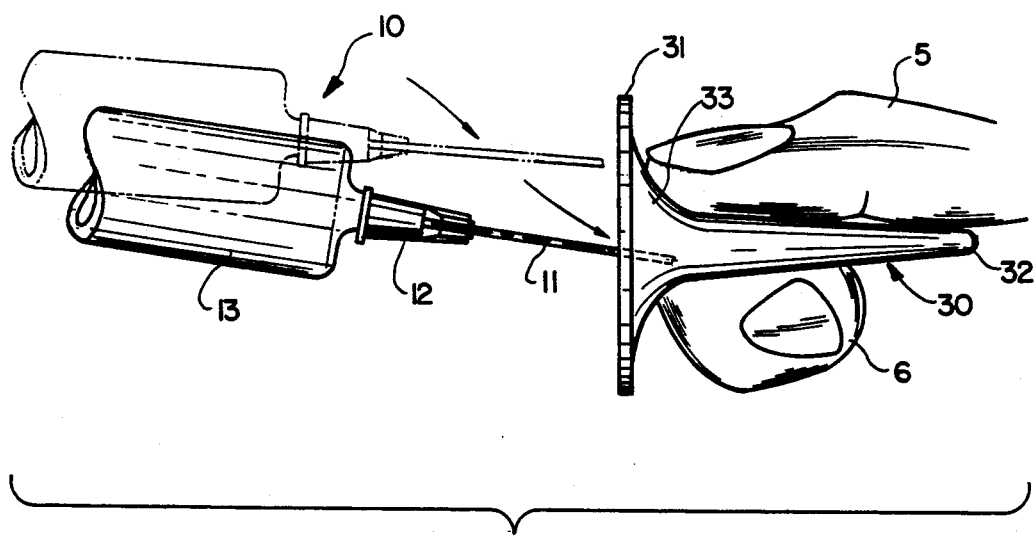
FIG. 2 is an environmental view of the present invention as it is intended to be used, providing maximum protection to the user's fingers during the recapping process.

As shown in the embodiment of the present invention, as illustrated in FIG. 2, the cannula cap 30 has a peripheral flange 31 about its opening. The cannula cap 30 also has a conically shaped needle housing region 32 and a funnel region 33 between the peripheral flange 31 and the needle housing region 32. The flange 31 extends out from the opening so as to provide a safety region S2 behind the flange 31. The safety region S2 is large enough to protect all of the fingers 5 and 6 used to grip the cannula cap 30. The front surface of the flange 31 is perpendicular to the direction the needle should be pointed if inserted down the needle housing region 32. If the needle 11 hits the flange 31 in a substantially perpendicular direction, the flange 31 will stop the advance of the needle since the needle will tend to embed in the flange 31. The flange 31, as well as the rest of the cannula cap 30, is preferably made of plastic which can not be penetrated by the needle 11.

As long as the fingers grip the cannula cap 30 about the funnel region 33, the fingers 5 and 6 will all be located behind the flange 31 and within the safety region S2. The funnel region 33 has an exterior surface which is concave to allow the user to easily grip the cannula cap 30. In this manner, the cannula cap is both safely and easily reinserted over the needle of the syringe 10.

Figure 3:
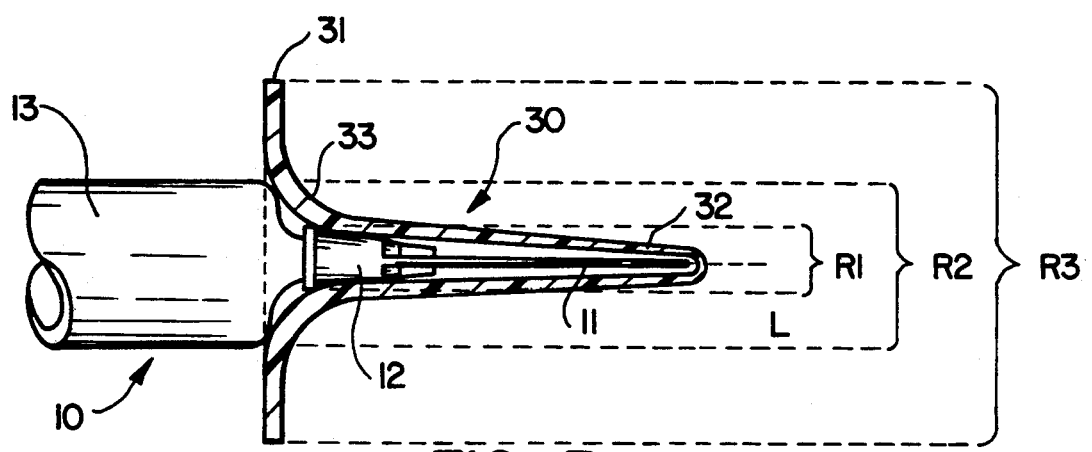
FIG. 3 is an elevated cross-sectional view of the present invention.

As shown in FIG. 3, once the needle 11 is inserted into the needle housing region 32, the hub 12 of the syringe 10 fits snugly about the opening of the needle housing region 32, in an airtight manner. In this manner, before the needle's use, the needle is maintained in its sterile condition, while after its use, contaminates from the ambient environment are prevented from entering the needle housing region once the cap 30 is reinserted over the needle.

As shown in the cross-sectional view of the cannula cap 30 in FIG. 3, the needle is maintained along a longitudinal center axis L of the cap 30. The opening of the needle housing region 32 extends out to a region R1 from the longitudinal center axis L of the cap 30. The funnel region 33 extends out from the region R1 to a region R2 from the longitudinal center axis L of the cap 30. The opening of the cannula cap 30 extends out to a region R2 from the longitudinal center axis L. The peripheral flange 31 extends from a region R2 to a region R3 about the opening of the cannula cap 30. In the preferred embodiment, the distance X between the regions R2 and R3 is about half an inch.

Figure 4:
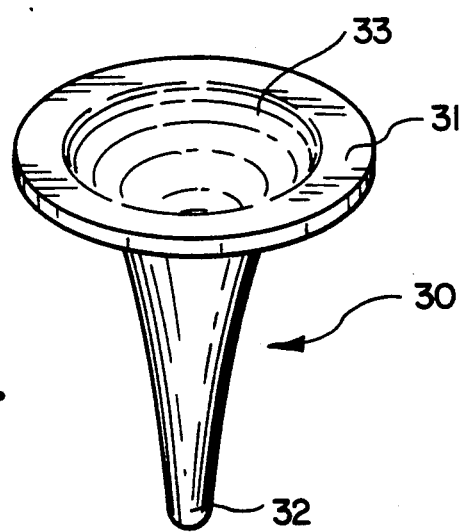
FIG. 4 is an elevated perspective view of the present invention.

The funnel region 33 of the cannula cap 30 begins at the opening of the cannula cap 30 and has a rounded inner surface (see FIGS. 2, 3 and 4). This inner surface guides the needle inserted through the opening of the cannula cap 30 to the opening of the needle housing region, when the needle is inserted in the cap opening outside of the region R1. Therefore, if the needle is directed in such a way as to fall within the region R3 but outside of the region R2 during the recapping process, in other words the user missed the cap opening all together, the needle 11 will impinge on the front outer surface of the peripheral flange 31. The needle will then embed therein and stop. As shown in FIG. 4, the peripheral flange 31 encompasses a circular region around the cap 30. In this manner, no portion of the user's finger 5 and 6 will be stuck by the needle 11 (also see FIG. 2).

However, if during the recapping process the user directs the needle to a region of the cap 30 between regions R1 and R2, the needle will impact the smooth rounded inner surface of the funnel region 33. Since the surface is rounded, the needle will bounce off the surface in a direction towards the longitudinal center axis L of the cap 30. In this manner the needle is thereby guided to the opening of the needle housing region 32. Once the needle is inserted through the opening of the needle housing region 32, the conical shape of needle housing region will direct the needle to the longitudinal center axis of the cap 30, since the circular diameter of each portion of the needle housing region decreases the closer the region is to the back closed end of the cannula cap.

It is to be understood that the present invention is not limited to the sole embodiment described above, but encompasses any and all embodiments within the scope of the following claims.

I claim:

1. In combination with a conventional syringe having a barrel and a needle attached to said barrel by a hub, a cannula cap comprising:

a conically shaped housing with an inner cavity extending from an open end to a closed end, said housing having circular cross-sections which progressively decrease in diameter relative to a longitudinal axis from said open end to said closed end;

said open end of said housing mating with said hub to provide an airtight cover for said needle;

a funnel integral with said conically shaped housing at said open end, said funnel having a smoothly rounded inner surface to slidably guide said needle into said housing, said inner surface extending along said longitudinal axis with a progressively increasing circular cross-section ending at an opening having a diameter sufficient to enclose and contact an outside surface of said barrel;

said inner surface at said opening being integral with a front planar surface of a peripheral flange, said front planar surface extending normal to said longitudinal axis a distance beyond said opening sufficient to cover and protect the fingers of a handler;

said funnel having an outer surface forming a smooth concave surface between a back planar surface of said peripheral flange and an outer surface of said housing, said back planar surface extending normal to said longitudinal axis beyond said opening a distance sufficient to cover and protect the fingers of said handler, said back planar surface forming a stop surface for the fingers of said handler when said handler grasps said cap by said funnel outer surface; whereby said funnel inner surface will guide said needle into said housing when said needle and said funnel are properly aligned, and said flange will receive needle jabs on said front planer surface of said flange when said needle and said funnel are not properly aligned, thereby protecting the fingers of said handler from said needle jabs.

2. A cannula cap as in claim 1, wherein said distance of said front planar surface and said back planar flange beyond said opening is at least one half inch.

3. A cannula cap as in claim 1 being formed of plastic material.

4. A cannula cap as in claim 2 being formed of plastic material.

* * * * *